US008623188B2

(12) United States Patent
Igarashi et al.

(10) Patent No.: US 8,623,188 B2
(45) Date of Patent: Jan. 7, 2014

(54) GAS SENSOR

(75) Inventors: Ai Igarashi, Konan (JP); Noboru Furuta, Kasugai (JP)

(73) Assignee: NGK Spark Plug Co., Ltd., Aichi (JP)

(*) Notice: Subject to any disclaimer, the term of this patent is extended or adjusted under 35 U.S.C. 154(b) by 90 days.

(21) Appl. No.: 13/281,314

(22) Filed: Oct. 25, 2011

(65) Prior Publication Data

US 2012/0103808 A1    May 3, 2012

(30) Foreign Application Priority Data

Oct. 26, 2010  (JP) .................................. 2010-239634
Sep. 20, 2011  (JP) .................................. 2011-204266

(51) Int. Cl.
*G01N 27/419*      (2006.01)
(52) U.S. Cl.
USPC ........... 204/424; 204/425; 204/426; 204/427; 204/428; 204/429; 73/23.31; 73/23.32
(58) Field of Classification Search
USPC ....................... 204/424–429; 73/23.31–23.32
See application file for complete search history.

(56) References Cited

U.S. PATENT DOCUMENTS

| 4,902,400 | A | * | 2/1990 | Usami et al. | 204/426 |
| 2001/0050229 | A1 | * | 12/2001 | Schnaibel et al. | 204/421 |
| 2004/0094416 | A1 | * | 5/2004 | Chen et al. | 204/426 |
| 2007/0084724 | A1 | * | 4/2007 | Mori et al. | 204/424 |

FOREIGN PATENT DOCUMENTS

| JP | 2003294687 A | 10/2003 |
| JP | 2009180634 A | 8/2009 |

* cited by examiner

*Primary Examiner* — Bach Dinh
(74) *Attorney, Agent, or Firm* — Sughrue Mion, PLLC

(57) ABSTRACT

A gas sensor including a plate-shaped laminate disposed in a housing and fixed thereto via an element passage member and formed by laminating a gas sensor element and a heating element. The gas sensor element includes a plate-shaped solid electrolyte member, and a pair of detection electrodes formed on front and back surfaces thereof and constituting, in cooperation with the solid electrolyte member, a detection section for detecting the concentration of a specific gas. Insulating substrates mainly composed of alumina are provided on opposite sides of the laminate in the laminating direction. Coating layers mainly composed of a first material higher in toughness than alumina are formed on at least portions of outer surfaces of the insulating substrates in the laminating direction, the portions facing the element passage member. The coating layers are not formed on surfaces of the laminate parallel to the laminating direction.

5 Claims, 2 Drawing Sheets

GAS SENSOR

TECHNICAL FIELD

The present invention relates to a gas sensor for detecting the concentration of a specific gas component of a gas to be measured (hereinafter referred to as an "object gas").

BACKGROUND ART

Conventionally, there has been known a gas sensor which detects the concentration of a specific gas component of an object gas, such as exhaust gas discharged from, for example, an automobile. Such a gas sensor uses a gas sensor element whose electrical characteristic changes in accordance with the concentration of the specific gas component of the object gas. A known gas sensor element is configured such that a pair of electrodes are formed on a solid electrolyte member mainly formed of zirconia, and an insulating layer, a heater, etc. are laminated thereon, whereby the gas sensor element assumes a plate-like outer shape as a whole.

In the above-described gas sensor element, the insulating layer is formed of ceramic whose predominant component is alumina, which is excellent in insulating property and heat resistance. The heater has a structure in which a heating resistor or the like is buried in a heater insulating layer formed of a ceramic material whose predominant component is alumina (for example, see Patent Document 1).

PRIOR ART DOCUMENT

Patent Document

[Patent Document 1] Japanese Patent Application Laid-Open (kokai) No. 2003-294687

DISCLOSURE OF THE INVENTION

Problems to be Solved by the Invention

In the above-described gas sensor element has the following problem. In a process of manufacturing the gas sensor element, particles of alumina, mullite, or the like may drop from a firing setter which is used during firing (such particles will be referred to debris of dropped particle). In this case, the debris of dropped particles may adhere to the surfaces of an unfired insulating layer and an unfired heater insulating layer provided on opposite sides of the gas sensor element with respect to the lamination direction (hereinafter, each of the unfired insulating layer and unfired heater insulating layer will be referred to as an unfired insulating substrate, and each of the insulating layer and the heater insulating layer will be referred to as an insulating substrate). The debris of dropped particles adhering to the surface of an unfired insulating substrate reacts with alumina, which is the predominant component of the insulating substrate during a firing stage, whereby particles of alumina grow anomalously, which causes a problem of lowering the breakage strength of the insulating substrate. Also, such a drop in the breakage strength of the insulating substrate raises the following problem. When the gas sensor element is assembled into a metallic shell and fixed thereto, the gas sensor element comes into contact with an element passage member such as a holder, a ceramic member (e.g., a sleeve), or a talc layer, which are disposed between the element and the metallic shell (housing) and into which the element is inserted. Thus, the pressure applied to the gas sensor element during the assembly may affect a contact portion of the gas sensor element, whereby the gas sensor element may be broken. Also, when measurement is performed by use of the gas sensor, due to vibration from an internal combustion engine or the like, the gas sensor element may come into contact with the element passage member, which may result in breakage of the gas sensor element.

The present invention has been accomplished in view of the foregoing, and an object of the present invention is to provide a gas sensor which can secure a required breakage strength even in the case where debris of particles dropped from a setter for firing in a manufacturing process adheres to the surface of an unfired gas sensor element, to thereby restrain occurrence of breakage of the gas sensor element.

Means for Solving the Problems

A gas sensor of the present invention includes a plate-shaped laminate which is disposed in a housing and fixed thereto via an element passage member and which is formed by laminating a gas sensor element and a heater having a heating element. The gas sensor element includes a plate-shaped solid electrolyte member, and a pair of detection electrodes formed on front and back surfaces of the solid electrolyte member and constituting, in cooperation with the solid electrolyte member, a detection section for detecting the concentration of a specific gas contained in an object gas. Insulating substrates containing alumina as a predominant component are provided on opposite sides of the laminate with respect to the lamination direction thereof. Coating layers containing, as a predominant component, a first material which is higher in toughness than alumina are formed on at least portions of outer surfaces of the insulating substrates with respect to the lamination direction, the portions facing the element passage member. The coating layers are not formed on surfaces of the laminate parallel to the lamination direction.

In the gas sensor element of the present invention having the above-described structure, coating layers containing, as a predominant component, a first material which is higher in toughness than alumina are formed on at least portions of the outer surfaces of the insulating substrates, which are provided on opposite sides of the laminate with respect to the lamination direction and which contain alumina as a predominant component, the portions facing the element passage member. By virtue of this configuration, the breakage strength of the portion on which the coating layers are provided can be increased. Therefore, even in the case where debris of particles dropped from a setter for firing in a manufacturing process adheres to the surface of the gas sensor element in an unfired state, a required breakage strength can be secured, whereby breakage of the gas sensor element during assembly to a housing can be restrained. Also, when measurement is performed by use of the gas sensor, due to vibration from an internal combustion engine or the like, the gas sensor element may come into contact with the element passage member. However, since a required breakage strength can be secured through provision of the coating layers, breakage of the gas sensor element can be restrained. Notably, the above-mentioned coating layers are not provided on the side surfaces (surfaces parallel to the lamination direction) of the laminate. Since the width of the gas sensor element is greater than the thickness thereof, a require breakage strength can be secured without provision of the coating layers on the surfaces parallel to the lamination direction. Therefore, even in the case where dropped particles or like debris is adhered to the surface of the gas sensor element in an unfired state, breakage of the gas sensor element can be retrained. Therefore, through omission of such coating layers, productivity is increased, and cost is lowered.

Notably, the phrase "insulating substrates containing alumina as a predominant component" means that the alumina content of the insulating substrates is 50% by mass or greater. Also, the phrase "coating layers containing, as a predominant component, a first material" means that the content of the first material of the coating layers is 50% by mass or greater.

Moreover, the phrase "a first material which is higher in toughness than alumina" means that the first material may be those which are higher in toughness than alumina defined by JIS R 1607 (1990). Examples of the first material include zirconia, silicon nitride, and silicon carbide.

Preferably, the thickness of the coating layers is set to fall within a range of 10 μm to 50 μm. When the thickness of the coating layers is equal to or greater than 10 μm, the effect of increasing breakage strength by the coating layers can be attained. Even when the thickness of the coating layers is increased to 20 μm, the breakage strength increasing effect hardly changes as compared with the case where the thickness is 10 μm. Also, in consideration of the fact that the gas sensor element is inserted into the element passage member, the upper limit of the thickness of the coating layers must be set to about 50 μm.

Preferably, the coating layers are formed of a material which is lower in thermal conductivity than the insulating substrates. By virtue of this, it become possible to reduce conduction of heat of the gas sensor element, which is heated by the heater, to the element passage member via the coating layers. Thus, the amount of electric power supplied to the heater can be reduced.

Preferably, the coating layers are formed of a material selected such that the difference in coefficient of thermal expansion between the material and the insulating substrates becomes $0.7 \times 10^{-6}$ or less. By virtue of this, separation of the coating layers from the insulating substrates can be prevented. Notably, when the difference in coefficient of thermal expansion between the coating layers and the insulating substrates exceeds $0.7 \times 10^{-6}$, this effect cannot be obtained in some cases.

Preferably, the coating layers contain zirconia as a predominant component. By virtue of this, the breakage strength of the portion on which the coating layers are provided can be increased. In addition, since zirconia is lower in volume resistivity than alumina. Therefore, generation of electrical leakage can be suppressed by not providing the above-mentioned coating layers on the side surfaces (surfaces parallel to the lamination direction) of the laminate.

Effect of the Invention

According to the present invention, there can be provided a gas sensor which can secure a required breakage strength even in the case where debris of particles dropped from a setter for firing in a manufacturing process adheres to the surface of an unfired gas sensor element, to thereby restrain occurrence of breakage of the gas sensor element when it is assembled into a housing.

MODE FOR CARRYING OUT THE INVENTION

Figure 1:
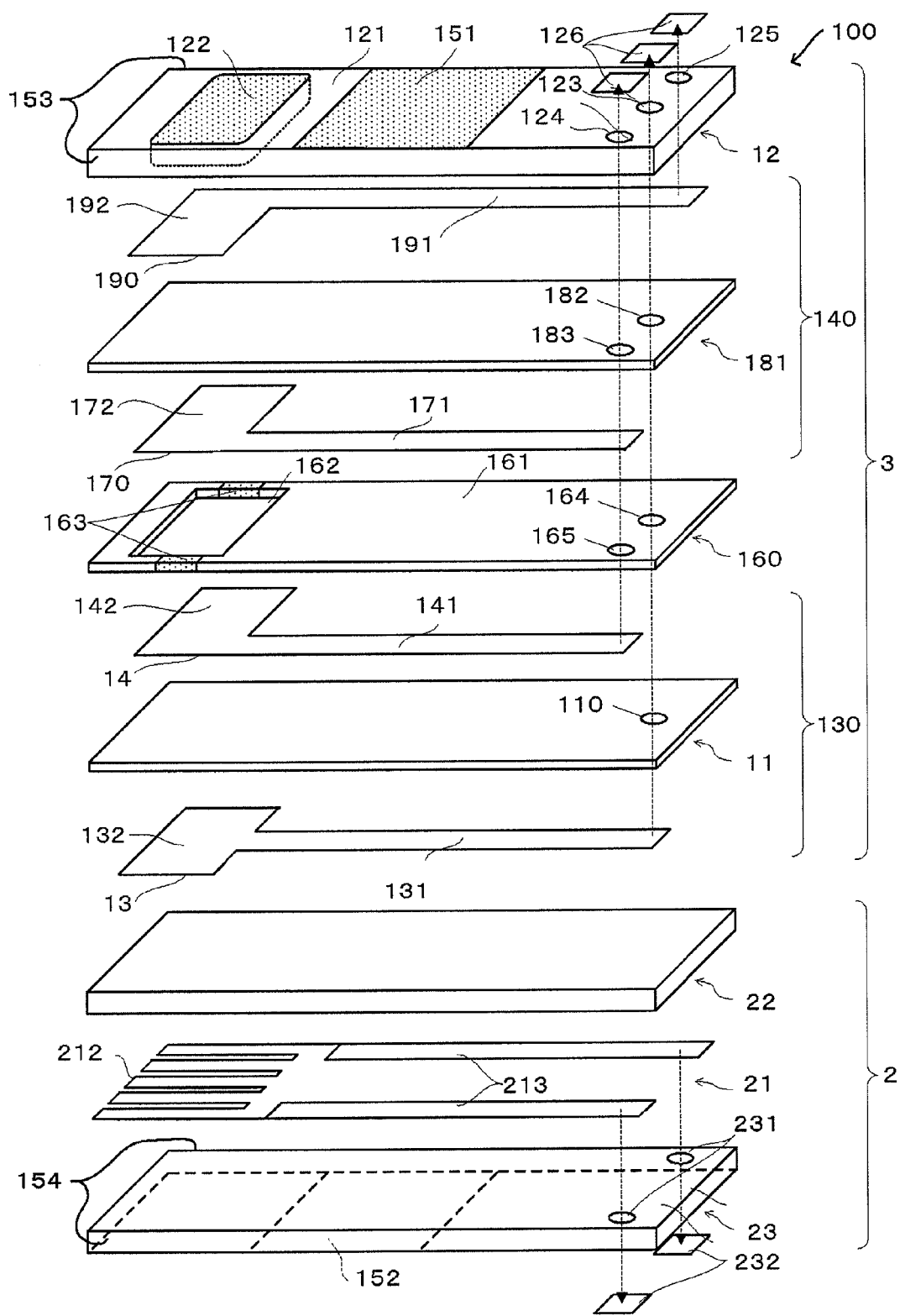
[FIG. 1] Exploded perspective view schematically showing the structure of a gas sensor element according to an embodiment of the present invention.

A laminate-type gas sensor element 100 according to an embodiment of the present invention will now be described with reference to the drawings. FIG. 1 is an exploded perspective view showing the structure of the gas sensor 100, which assumes a platelike shape as a whole. The gas sensor element 100 is configured by stacking a gas sensor element main body 3 and a heater 2 in layers.

The gas sensor element main body 3 includes an oxygen concentration detection cell 130 and an oxygen pump cell 140. A gas detection chamber forming layer 160 is provided between the oxygen concentration detection cell 130 and the oxygen pump cell 140, and a protection layer 12 is provided on the outer side (the upper side in the drawing) of the oxygen pump cell 140.

The oxygen concentration detection cell 130 includes a solid electrolyte member 11, and a reference electrode 13 and a detection electrode 14 formed on the opposite surfaces, respectively, of the solid electrolyte member 11. The solid electrolyte member 11 has oxygen ion conductivity and is formed of a zirconia ($ZrO_2$) sintered body or an $LaGaO_3$ sintered body containing yttria ($Y_2O_3$) or calcia (CaO) added thereto as a stabilizer. The solid electrolyte member 11 is used for an oxygen concentration cell. In the present embodiment, the solid electrolyte member 11 is formed of a zirconia sintered body containing yttria added thereto as a stabilizer, and also containing alumina (10 to 80% by mass).

The reference electrode 13, which is formed of a porous material, is formed on the surface of the solid electrolyte member 11 facing the heater 2. The detection electrode 14, which is also formed of a porous material, is formed on the surface of the solid electrolyte member 11 opposite the reference electrode 13. The reference electrode 13 and the detection electrode 14 respectively have a reference electrode portion 132 and a detection electrode portion 142, which face each other and which constitute a detection section in cooperation with the solid electrolyte member 11. A reference electrode lead portion 131 and a detection electrode lead portion 141 extend along the longitudinal direction of the solid electrolyte member 11 from the reference electrode portion 132 and the detection electrode portion 142, respectively. The reference electrode portion 132, the detection electrode portion 142, the reference electrode lead portion 131, the detection electrode lead portion 141 are formed of, for example, Pt or the like.

The oxygen pump cell 140 includes a second solid electrolyte member 181, and a third electrode 170 and a fourth electrode 190 formed on the opposite sides, respectively, of the second solid electrolyte member 181. The third electrode 170 and the fourth electrode 190 respectively have a third electrode portion 172 and a fourth electrode portion 192, which face each other and which constitute a detection section in cooperation with the second solid electrolyte member 181. A third lead portion 171 extends from the third electrode portion 172 in the longitudinal direction of the second electrolyte member 181, and a fourth lead portion 191 extends from the fourth electrode portion 192 in the longitudinal direction of the second electrolyte member 181.

The gas detection chamber forming layer 160 provided between the oxygen pump cell 140 and the oxygen concentration detection cell 130 is composed of an insulating portion 161 and diffusion rate limiting portions 163. A gas detection chamber 162 is formed in the insulating portion 161 of the gas detection chamber forming layer 160 at a position corresponding to the detection electrode portion 142 and the third electrode portion 172. This gas detection chamber 162 communicates with the atmosphere outside the sensor element via communication portions of the gas detection chamber forming layer 160 located on opposite sides of the gas detection chamber 162 with respect to the width direction thereof. The diffusion rate limiting portions 163 are disposed in the communication portions so as to enables the object gas from the outside atmosphere to diffuse into the gas detection chamber 162 at a predetermined limited speed.

No limitation is imposed on the material of the insulating portion 161 so long as it is formed of a ceramic sintered body having insulating properties. Examples of the material of the insulating portion 161 include oxide ceramics such as alumina or mullite. The diffusion rate limiting portions 163 are formed of porous alumina. The diffusion rate limiting portions 163 limit the speed at which the object gas flows into the gas detection chamber 162.

Notably, the end of the reference electrode lead portion 131 is electrically connected to one of three signal takeout terminals 126 via a through hole 110 provided in the solid electrolyte member 11, a through hole 164 provided in the insulating layer 160, a through hole 182 provided in the second solid electrolyte member 181, and a through hole 123 provided in the protection layer 12. The end of the detection electrode lead portion 141 is electrically connected to another of the signal takeout terminals 126 via a through hole 165 provided in the insulating layer 160, a through hole 183 provided in the second solid electrolyte member 181, and a through hole 124 provided in the protection layer 12.

Also, the end of the third lead portion 171 is connected to one signal takeout terminal 126 via the through hole 183 provided in the second solid electrolyte member 181 and the through hole 124 provided in the protection layer 12. The end of the fourth lead portion 191 is connected to another signal takeout terminal 126 via a through hole 125 provided in the protection layer 12. Notably, the detection electrode lead portion 141 and the third lead portion 171 are connected together via the through hole 165 so that they have the same potential.

The heater 2 includes a heating resistor 21, which is sandwiched between a first insulating substrate 22 and a second insulating substrate 23 (corresponding to the "insulating substrate" of the claims), which are formed of a ceramic sintered body of alumina, which is excellent in insulation properties. The heating resistor 21 has a heat generation portion 212 formed into a meandering shape, and a pair of heater lead portions 213 connected to opposite ends of the heat generation portion 212 and extending along the longitudinal direction. End portions of the heater lead portions 213 opposite the side where they are connected to the heat generation portion 212 are electrically connected to a pair of heater electricity supply terminals 232 via two through holes 231, which penetrate the second insulating substrate 23. The heater electricity supply terminals 232 are connected to external terminals for connection of an external circuit.

The heating resistor 21 may be formed of noble metal, tungsten, molybdenum, or the like. Examples of noble metal include Pt, Au, Ag, Pd, Ir, Ru, and Rh. Only one of these noble metals may be used, or two or more of these noble metals may be used in combination. Notably, preferably, the heating resistor 21 is mainly formed of a noble metal from the viewpoint of heat resistance, oxidation resistance, etc. More preferably, the heating resistor 21 is mainly formed of Pt. Also, desirably, the heating resistor 21 contains a ceramic component, in addition to the noble metal which mainly constitutes the heating resistor 21. From the viewpoint of bonding strength, preferably, the heating resistor 21 contains, as a ceramic component, the same component as the predominant component (alumina in the present embodiment) of the first and second ceramic insulating substrates 22 and 23 in which the heating resistor 21 is buried.

In the heating resistor 21, the heat generation portion 212 is a portion which generates heat upon supply of electricity thereto, and the lead portions 213 are portions which convey an externally supplied DC voltage to the heat generation portion 212 and which hardly generate heat. No limitation is imposed on the shapes of the heat generation portion 212 and the lead portions 213. For example, the heat generation portion 212 may have a width smaller than that of the lead portions 213, and have a meandering shape so that the heat generation portion 212 has a denser pattern as compared with the lead portions 213.

The protection layer 12 includes a porous electrode protection layer 122 which is formed on the surface of the fourth electrode portion 192 and protects the fourth electrode portion 192 from poisoning, and a reinforcing protection layer (corresponding to the "insulating substrate" the claims 121 which is formed on the surface of the fourth lead portion 191 and protects the second solid electrolyte member 181. This reinforcing protection layer 121 is formed of a ceramic sintered boy of alumina.

In the gas sensor element 100 constituted by laminating the gas sensor element main body 3 and the heater 2, the reinforcing protection layer 121 formed of alumina and the second insulating substrate 23 formed of alumina are located on the opposite sides of the gas sensor element 100 with respect to the lamination direction thereof (the upper and lower sides in FIG. 1). Coating layers 151 and 152 are formed on at least portions of the respective outer surfaces of the reinforcing protection layer 121 and the second insulating substrate 23 with respect to the lamination direction (in FIG. 1, the upper surface of the reinforcing protection layer 121 and the lower surface of the second insulating substrate 23), the portions facing a member through which the gas sensor element 100 is passed (hereinafter referred to as the "element passage member") (specifically, a metallic holder 34, a ceramic holder 35, a talc layer 36, and a sleeve 39). In the present embodiment, the coating layers 151 and 152 are formed to extend from a point about 12 mm away from the front end of the gas sensor element 100, to a point about 30 mm away from the front end of the gas sensor element 100. Such a coating layer is not formed on the side surfaces 153 of the reinforcing protection layer 121 and the side surfaces 154 of the second insulating substrate 23, which are parallel to the lamination direction of the laminate. Similarly, such a coating layer is not formed on the side surfaces of the second solid electrolyte member 181, the side surfaces of the gas detection chamber forming layer 160, the side surfaces of the solid electrolyte member 11, and the side surfaces of the first insulating substrate 22.

The coating layers 151 and 152 contain zirconia as a predominant component, and may be formed, for example, through a process of applying, through printing, paste containing zirconia (about 50%) to portions of an unfired laminate where the coating layers 151 and 152 are to be formed, flowed by dewaxing and firing performed for the coating layers 151 and 152 along with the laminate. Notably, in addition to zirconia, the coating layers 151 and 152 may contain insulating ceramics such as alumina, mullite, or titania.

A porous protection layer (not shown) is formed on a front end portion of the gas sensor element 100, which is constituted by laminating the gas sensor element main body 3 and the heater 2, the front end portion being exposed to the object gas, such that the porous protection layer covers the entire circumference of the front end portion.

In the gas sensor element 100, which includes the oxygen pump cell 140 and the oxygen concentration detection cell 130 as described above, oxygen contained in the object gas within the gas detection chamber 162 can be pumped out and oxygen can be pumped thereinto by making use of the oxygen pumping action of the oxygen pump cell 140; and oxygen concentration can be measured by making use of the concentration cell action of the oxygen concentration detection cell 130. Therefore, the gas sensor element 100 can be used as an air-fuel-ratio sensor or the like.

Figure 2:
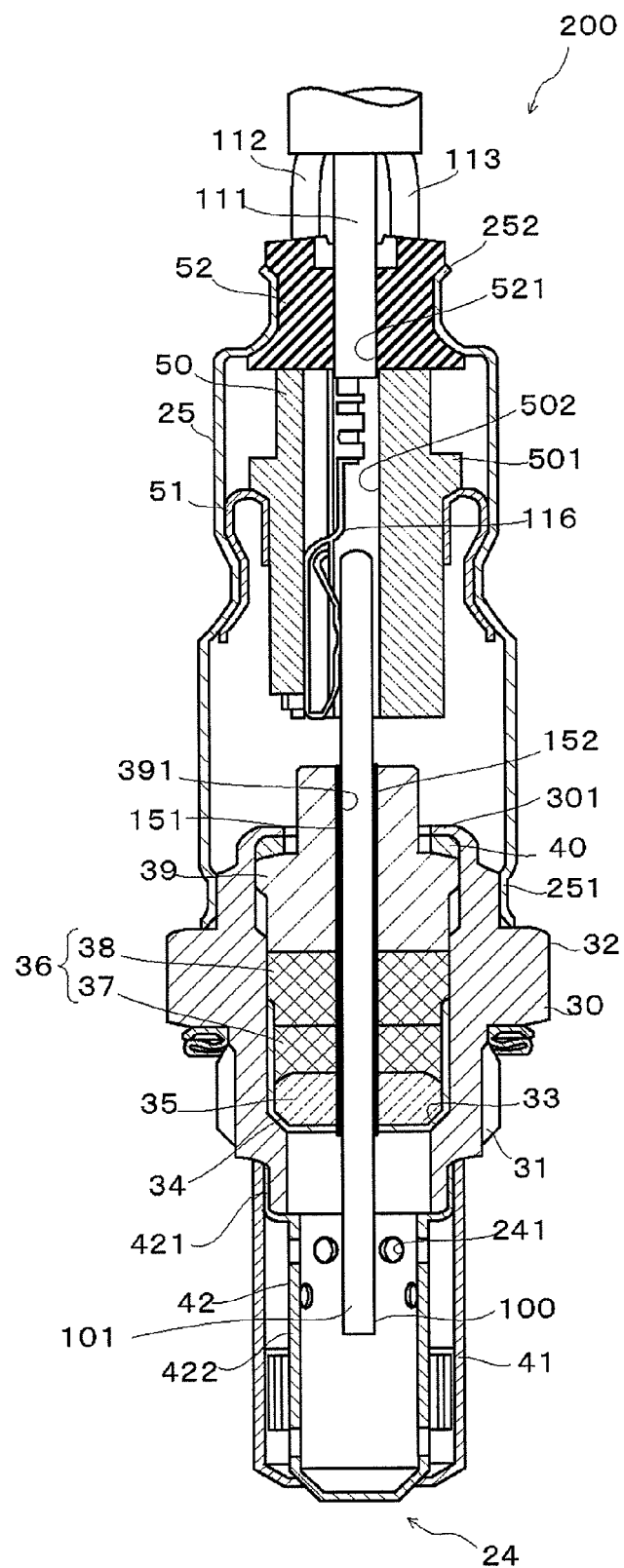
[FIG. 2] Cross-sectional view showing the structure of a gas sensor according to the embodiment of the present invention.

FIG. 2 is an overall cross-sectional view showing an example of a gas sensor into which the above-described gas sensor element 100 is incorporated; specifically, a gas sensor 200 which is attached to an exhaust pipe of an internal combustion engine and used for, for example, measurement of oxygen concentration of exhaust gas.

The metallic shell (housing) 30 shown in FIG. 2 has an external thread portion 31 for mounting the gas sensor onto the exhaust pipe, and a hexagonal portion 32, with which a mounting tool is engaged when the gas sensor is to be mounted. The metallic shell 30 also has a shell side step portion 33 projecting radially inward. This shell side step portion 33 supports a metallic holder 34 for holding the gas sensor element 100. The above-mentioned ceramic holder 35 and the talc layer 36, which dispose the gas sensor element 100 at a predetermined position, are disposed inside the metallic holder 34 in this sequence from the front end side.

The talc layer 36 is composed of a first talc layer 37 disposed inside the metallic holder 34, and a second talc layer 38 projects from the rear end of the metallic holder 34. The above-mentioned sleeve 39, which is formed of alumina, is disposed on the rear end side of the second talc layer 38. This sleeve 39 is a cylindrical member having a plurality of cylindrical portions of different diameters. The sleeve 39 has an axial hole 391 extending along the axis thereof, and the gas sensor element 100 is passed through the axial hole 391. A rear-end-side crimp portion 301 of the metallic shell 30 is bent inward, whereby the sleeve 39 is pressed toward the front end side of the metallic shell 30 via a ring member 40 formed of stainless steel.

The above-described coating layers 151 and 152 formed on the surface of the gas sensor element 100 are located in a region extending from the front end of the metallic holder 34 to the rear end of the sleeve 39; i.e., they face the metallic holder 34, the ceramic holder 35, the talc layer 36, and the sleeve 39.

Also, a protector 24 is attached, through welding, to the outer circumference of a front end portion of the metallic shell 30 so as to cove a front end portion 101 of the gas sensor element 100 projecting from the front end of the metallic shell 30. The protector 24 is formed of metal, and has a plurality of gas introduction holes 241. The protector 24 has a double structure; i.e., is composed of an outer protector 41 and an inner protector 42. The outer protector 41 has a bottomed, cylindrical tubular shape and has a constant outer diameter. The inner protector 42 has a bottomed, cylindrical tubular shape, and its rear end portion 421 is greater in outer diameter than its front end portion 422.

Meanwhile, a front end portion of an outer cover 25 is fitted onto a rear end portion of the metallic shell 30. A front end portion 251 of the outer cover 25, whose diameter is increased on the front end side thereof, is fixed to the metallic shell 30 by means of laser welding or the like. A separator 50 is disposed inside a rear end portion of the outer cover 25, and a holding member 51 is provided in the clearance between the separator 50 and the outer cover 25. This holding member 51 is in engagement with a projecting portion 501 of the separator 50, and is fixedly held between the outer cover 25 and the separator 50 when the outer cover 25 is crimped.

The separator 50 has through holes 502 extending from the front end to rear end thereof. Lead wires 111 to 115 of the gas sensor element 100 (FIG. 2 shows the lead wires 111 to 113 only) are inserted into the through holes 502. Connection terminals 116 for connecting the lead wires 111 to 115 to the external terminals of the gas sensor element 100 are accommodated in the through holes 502. The lead wires 111 to 115 are connected to an unillustrated outside connector. Electrical signals are transmitted between the lead wires 111 to 115 and external equipment such as an ECU via the connector. Although not illustrated in detail, each of the lead wires 111 to 115 has a structure in which a conductor is covered with an insulative coating formed of resin.

Furthermore, a rubber cap 52 having a generally circular columnar shape is disposed on the rear side of the separator 50 so as to close a rear end opening 252 of the outer cover 25. This rubber cap 52 is fixed to the outer cover 25 through a process of crimping the outer cover 25 radially inward in a state in which the rubber cap 52 is placed inside the rear end of the outer cover 25. The rubber cap 52 also has through holes 521 extending from the front end to rear end thereof. The lead wires 111 to 115 are passed through the through holes 521.

In the gas sensor 200 of the present embodiment having the above-described structure, as shown in FIGS. 1 and 2, the coating layers 151 and 152, whose predominant component is zirconia that is higher in toughness than alumina, are formed on at least portions of the respective outer surfaces of the reinforcing protection layer 121 and the second insulating substrate 23 (in FIG. 1, the upper surface of the reinforcing protection layer 121 and the lower surface of the second insulating substrate 23), which are the outermost layers of the laminate that constitutes the gas sensor element 100, the portions facing the element passage member such as the metallic holder 34, the ceramic holder 35, the talc layer 36, and the sleeve 39. By virtue of this configuration, even in the case where, during firing of the gas sensor element 100, debris of particles dropped from a setter for firing adheres to the surface of the gas sensor element 100 in an unfired state, a required breakage strength can be secured, whereby breakage of the gas sensor element 100 during assembly to the metallic shell 30 can be restrained. Also, when measurement is performed by use of the gas sensor 200, due to vibration from an internal combustion engine or the like, the gas sensor element 100 may come into contact with the element passage member. However, since a required breakage strength can be secured through provision of the coating layers 151 and 152, breakage of the gas sensor element 100 can be restrained.

Actually, two lots of gas sensor elements (each lot includes 30 gas sensor elements) were manufactured as each of Examples 1 to 8 and Comparative Example 1 (in total, 540 gas sensor elements were manufactured), and the breakage strength of each gas sensor element was measured. As Examples 1 to 8, there were manufacture gas sensor elements in which the coating layers 151 and 152 were formed by applying the material of the layers one time (Examples 1 to 4) and gas sensor elements in which the coating layers 151 and 152 were formed by applying the layer material two times (Examples 5 to 8). For one lot of the gas sensor elements manufactured as each of Examples 1 to 8 and Comparative Example 1, breakage strength was measured for the case where a foreign object equivalent to debris of particles dropped from the setter for firing adhered to the gas sensor elements. For the other lot of the gas sensor elements manufactured as each of Examples 1 to 8 and Comparative Example 1, breakage strength was measured for the case where a foreign object equivalent to debris of particles dropped from the setter for firing did not adhere to the gas sensor elements. Notably, a three-point bending test was employed so as to measure breakage strength. The three-point bending test was performed as follows. A span of 20 mm was set on each gas sensor element, and a gauge was lowered at a speed of 10 mm/min toward the center of the span (a portion where the coating layers 151 and 152 were provided). A load value at the time when the gas sensor element was broken was obtained. The average load value was obtained for each of Examples and Comparative Example.

In the case where a foreign object equivalent to debris of particles dropped from the setter for firing adhered to the gas sensor elements, when the average breakage strength of Comparative Example 1 was considered 1, the average breakage strength of Examples 1 to 8 was about 1.09, and was about 9% higher than that of Comparative Example 1. As to the average breakage strength, there was no significant difference between Examples 1 to 4 (in which the layer material was applied one time) and Examples 5 to 8 (in which the layer material was applied two times).

In the case where a foreign object equivalent to debris of particles dropped from the setter for firing did not adhere to the gas sensor elements, when the average breakage strength of Comparative Example 1 was considered 1, the average breakage strength of Examples 1 to 8 was about 1.15, and was about 15% higher than that of Comparative Example 1. As to the average breakage strength, there was no significant difference between Examples 1 to 4 (in which the layer material was applied one time) and Examples 5 to 8 (in which the layer material was applied two times).

As shown in the above-described Examples, it was confirmed that the gas sensor elements of Examples 1 to 8 which have the coating layers 151 and 152 containing zirconia as a predominant component exhibit higher breakage strength as compared with those of Comparative Example 1 which do not have the coating layers.

Notably, in the present embodiment, the coating layers 151 and 152 are not provided on the side surfaces (surfaces parallel to the lamination direction) of the laminate that constitutes the gas sensor element 100. Since the width of the gas sensor element 100 is greater than the thickness thereof, a require breakage strength can be secured without provision of the coating layers 151 and 152 on the surfaces parallel to the lamination direction. Therefore, even in the case where dropped particles or like debris is adhered to the surface of the gas sensor element 100 in an unfired state, breakage of the gas sensor element 100 can be retrained. Therefore, through omission of such coating layers, productivity is increased, and cost is lowered.

Notably, in the case where the coating layers 151 and 152 were formed by applying the layer material one time, the thickness of the coating layers 151 and 152 became about 10 µm, and, in the case where the coating layers 151 and 152 were formed by applying the layer material two times, the thickness of the coating layers 151 and 152 became about 20 µm. However, as to breakage strength, no difference was observed between the two cases. In consideration of the fact that the gas sensor element is inserted into the element passage member, the upper limit of the thickness of the coating layers 151 and 152 must be set to about 50 µm. Therefore, preferably, the thickness of the coating layers 151 and 152 falls within a range of 10 µm to 50 µm, inclusive.

The coating layers 151 and 152 are formed of a material which is lower in thermal conductivity than the reinforcing protection layer 121 and the second insulating substrate 23. Therefore, it is possible to reduce conduction of heat of the gas sensor element 100, which is heated by the heater 2, to the element passage member via the coating layers 151 and 152. Thus, the amount of electric power supplied to the heater 2 can be reduced.

Preferably, the difference in coefficient of thermal expansion between the coating layer 151 (152) and the reinforcing protection layer 121 or the second insulating substrate 23 is $0.7 \times 10^{-6}$ or less. Thus, it is possible to prevent separation of the coating layer 151 (152) from the reinforcing protection layer 121 or the second insulating substrate 23. Notably, in the present embodiment, the coefficient of thermal expansion of the coating layers 151 and 152 is $8.7 \times 10^{-6}$, and the coefficient of thermal expansion of the reinforcing protection layer 121 and the second insulating substrate 23 is $8.6 \times 10^{-6}$.

Since the predominant component of the coating layers 151 and 152 is zirconia, the breakage strength of a portion on which the coating layers 151 and 152 are provided can be increased. In addition, since zirconia is lower in volume resistivity than alumina. Therefore, generation of electrical leakage can be suppressed by not providing the above-mentioned coating layers 151 and 152 on the side surfaces (surfaces parallel to the lamination direction) of the laminate.

Although the present invention has been described on the basis of the above-described embodiment, the present invention is not limited to the embodiment, and may be modified freely without departing from the scope of the invention. For example, in the embodiment, the coating layers 151 and 152 are formed of a material containing zirconia as a predominant component. However, the material of the coating layers 151 and 152 is not limited thereto, and the coating layers 151 and 152 may be mainly formed of a first material which is higher in toughness than alumina. For example, the first material may be those which are higher in toughness than alumina defined by JIS R 1607 (1990). More specifically, the coating layers 151 and 152 may be formed of a material whose predominant component is silicon nitride or silicon carbide.

In the above-described embodiment, the reinforcing protection layer 121 and the second insulating substrate 23 are formed of alumina. However, their may be formed of another material so long as the material contains alumina as a predominant component. The material may also contain zirconia and/or mullite.

The present invention can be applied to a laminate-type gas sensor element used in gas sensors other than the air-fuel-ratio sensor, such as an HC sensor, a CO sensor, and an NOx sensor.

DESCRIPTION OF REFERENCE NUMERALS

2 . . . heater; 3 . . . gas sensor element main body; 11 . . . solid electrolyte member; 13 . . . reference electrode; 14 . . . detection electrode; 21 . . . heating resistor; 23 . . . second insulating substrate; 100 . . . gas sensor element; 121 . . . reinforcing protection layer; 151, 152 . . . coating layer; 153, 154 . . . side surface; 200 . . . gas sensor

The invention claimed is:

1. A gas sensor comprising a plate-shaped laminate which is disposed in a housing and fixed thereto via an element passage member and which is formed by laminating a gas sensor element having a major dimension extending in a longitudinal direction and a heater having a heating element, the gas sensor element comprising:
a plate-shaped solid electrolyte member; and
a pair of detection electrodes formed on front and back surfaces of the solid electrolyte member and constituting, in cooperation with the solid electrolyte member, a detection section for detecting the concentration of a specific gas contained in an object gas, wherein first and second insulating substrates containing alumina as predominant component are provided on opposite sides of the laminate with respect to the lamination direction thereof;

the first insulating substrate is a protection layer comprising a reinforcing protection layer and a porous electrode protection layer, the porous electrode protection layer protecting the detection electrode formed on the front surface of the solid electrolyte member, said reinforcing protection layer having a width equal to that of the solid electrolyte member in a direction perpendicular to the longitudinal direction of the gas sensor element, first and second coating layers containing, as a predominant component, a first material which is higher in toughness than alumina are formed on at least portions of outer surfaces of the first and second insulating substrates with respect to the lamination direction, respectively, the portions facing the element passage member;

the coating layer formed on the first insulating substrate is formed throughout the entire width of the reinforcing protection layer;

the coating layers are not formed on surfaces of the laminate parallel to the lamination direction; and wherein the first and second insulating substrates are outermost members of the laminate and the first and second coating layers are directly formed on at least portions of outer surfaces of the first and second insulating substrates, respectively.

2. A gas sensor according to claim 1, wherein the thickness of the coating layers falls within a range of 10 μm to 50 μm.

3. A gas sensor according to claim 1, wherein the coating layers are formed of a material which is lower in thermal conductivity than the insulating substrates.

4. A gas sensor according to claim 1, wherein the coating layers are formed of a material selected such that the difference in coefficient of thermal expansion between the material and the insulating substrates becomes $0.7 \times 10^{-6}$ or less.

5. A gas sensor according to claim 1, wherein the coating layers contain zirconia as a predominant component.

* * * * *